(12) United States Patent
Conrad et al.

(10) Patent No.: US 6,635,435 B1
(45) Date of Patent: Oct. 21, 2003

(54) FLUOROGENIC SUBSTRATES AND THEIR USE

(75) Inventors: Michael J. Conrad, Escondido, CA (US); Liyan He, Escondido, CA (US)

(73) Assignee: Chromagen, Inc., San Diego, CA (US)

( * ) Notice: Subject to any disclaimer, the term of this patent is extended or adjusted under 35 U.S.C. 154(b) by 0 days.

(21) Appl. No.: 09/350,461

(22) Filed: Jul. 9, 1999

Related U.S. Application Data
(60) Provisional application No. 60/092,245, filed on Jul. 10, 1998.

(51) Int. Cl.$^7$ ................................................. C12Q 1/34
(52) U.S. Cl. ............................ 435/18; 435/23; 536/4.1
(58) Field of Search ........................ 435/18, 23; 536/4.1

(56) References Cited

U.S. PATENT DOCUMENTS

| | | | |
|---|---|---|---|
| 4,585,598 A | | 4/1986 | Harnisch ..................... 558/196 |
| 4,614,713 A | | 9/1986 | Harnisch ..................... 435/21 |
| 4,844,841 A | | 7/1989 | Koller et al. ................. 562/55 |
| 5,086,129 A | * | 2/1992 | Kohler et al. ............... 525/537 |
| 5,132,432 A | | 7/1992 | Haugland et al. ........... 548/518 |
| 5,272,260 A | | 12/1993 | Pope et al. ................. 536/18.1 |
| 5,424,440 A | | 6/1995 | Klem et al. ................. 548/114 |
| 5,701,323 A | * | 12/1997 | Kahr et al. |

FOREIGN PATENT DOCUMENTS

WO  9315097  8/1993

OTHER PUBLICATIONS

HCAPLUS abstract (Acc No 1968:486693). Gerasimenko et al. (1968). Chemistry of pyrene. Zh. Org. Khim., 4(8), pp 1473–1477.*

Nito S. Identification of Phenolic Compounds in Fly Ash From Municipal Waste Inceneration by Gas Chromatography and Mass Spectrometry. Chemosphere 33(11)2239–2253, 1996.*

Shou M. Regioselective and Stereoselective Metabolisms of Pyrene and 1–Bromopyrene by Rat Liver Microsomes and Effects of Enzyme Inducers. Drug Metabolism and Dispostion 16(2)173–183, 1988.*

Sato, Eisuke, Kazuyoshi Chiba, Motonori Hoshi, Yuichi Kanaoka (1992) "Pyranine Phosphate as a New Fluorogenic Substrate for Acidic and Alkaline Phosphatases" *Chem. Pharm. Bull* 40(3):786–788.

Wolfbeis, Otto S., Eva Furlinger, Herbert Kroneis, Hermann Marsoner (1983) "Fluorimetric Analysis: A Study on Fluorescent Indicators for Measuring Near Neutral ("Physiological") pH–Values" *Anal. Chem.* 314:119–124.

Koller, Ernst (1994) "Fluorogenic substrates for enzymes analysis" *Amer. Biotech. Laboratory* 13(Nov):13–15.

Tietze and Bayer (1937) from the Wissenschaftl Hauptlaboratorium of I.G. Garbenindustrie–Werk Leverkunsen, Printed in Germany–Druck: Metzger & Wittig, Leipzig, pp. 189–210.

Turro, N.J. (1978) "Modern Molecular Photochemistry", The Benjamin/Cummings Publishing Co., Inc., pp. 110–111.

Wolfbeis, Otto S. and Ernst Koller (1983) "Fluorimetric Assay of Hydrolases at Longwave Excitation and Emission Wavelengths with New substrates Possessing Unique Water Solubility" *Analytical Biochemistry* 129:365–370.

Rifani, Michael, Yi–Yian Yin, D.S. Elliott (1995) "Solid State Dye Lasers from Stereospecific Host—Guest Interactions" *J. Am. Chem. Soc.* 117:7572–7573.

Li, Tiechao, Richard Giasson (1994) "Synthesis and Characterization of Functionalized Analogs of 1, 3, 6, 8–Tetrakis(methylsulfanyl)pyrene and Their Electron–Conducting Radical–Cation Salts" *J. Am. Chem. Soc.* 116:9890–9893.

Gerasimenko, E. Y., N. T. Potelsehchenko (1968) "Chemistry of pyrene. VI. 1, 6, 8–Trichloro–2, 3–phthaloylpyrene" *Chemical Abstracts*, vol 69, No. 86693.

* cited by examiner

*Primary Examiner*—Ralph Gitomer
(74) *Attorney, Agent, or Firm*—Saliwanchik, Lloyd & Saliwanchik

(57) ABSTRACT

The subject invention provides compounds useful as fluorogenic substrates. Upon hydrolysis of a hydrolyzable group, a halo-pyrene substituted molecule is developed which is highly fluorescent, water soluble and exhibits several desirable characteristics, including a large Stokers' shift.

9 Claims, 7 Drawing Sheets

FLUOROGENIC SUBSTRATES AND THEIR USE

CROSS-REFERENCE TO A RELATED APPLICATION

This application claims priority to U.S. provisional application Serial No. 60/092,245, filed Jul. 10, 1998.

FIELD OF THE INVENTION

This invention relates to the field of fluorescent substrates for hydrolytic enzymes, and also relates to the field of biological assays.

BACKGROUND OF THE INVENTION

In the field of biomolecular analysis, labeling with either radioactive isotopes or colorimetric dyes have historically been the detection methods of choice. However, due to the difficulties of working with radioactive isotopes and the limits of sensitivity of colored dyes, there is an increasing interest in the use of luminescent molecules for labeling and detection. In particular, there is increasing interest in developing luminescent detection systems that not only offer greater sensitivity than radioactive or colorimetric detection but also enable simultaneous detection of multiple analytes in the same sample.

Two types of luminescence are of general interest in biological assays: chemiluminescence and fluorescence. Chemiluminescence is the transient release of energy as light during a chemical reaction, which in most cases of biological interest involves a reaction catalyzed by a specific enzyme. Fluorescence is the emission of light induced by excitation of a molecule with light of a different wavelength. Unlike chemiluminescence, a fluorescent molecule can be derivatized so that it can be used either (i) to covalently attach an already fluorescent molecule as a label, or, (ii) as a "fluorogenic" enzyme substrate which can be converted, by action of a specific enzyme, into a fluorescent product which exhibits greatly enhanced fluorescence as compared to the starting substrate. In either case, detection relies upon the indirect detection of a specific enzyme by measurement of the rate or extent to which a substrate for that enzyme has been converted into a detectable chemiluminescent or fluorescent final product.

In biological assays, the activity of an enzyme is used to indirectly detect or measure the quantity of a complementary biological "target." The enzymes most commonly used for this purpose are Alkaline Phosphatase, β-Galactosidase, β-Glucuronidase, β-Glucosidase and Horse Radish Peroxidase. With the exception of HRP, the first four enzymes form a related set in that all four are hydrolytic enzymes that act on substrate molecules which have been derivatized at hydroxyl moieties to create the phosphoric acid, galactoside, glucoside and glucuronide substrates, respectively. The hydrolytic enzymes are widely used with calorimetric and chemiluminescent substrates and, despite the sensitivity limitations of current fluorogenic substrates, are also in widespread use, most commonly the substrates of 4-Methyl Umbelliferone (4MU) and Attophos. By contrast, although HRP is an important non-hydrolytic enzyme for both histochemistry and ELISAs using colorimetric and chemiluminescent substrates, fluorogenic peroxidase substrates are not extensively used for detection owing to their insufficient stability in aqueous solutions.

Numerous new chemiluminescent enzyme substrates for hydrolytic enzymes have been developed during the past decade as a result of which the advantages and limitations of chemiluminescent systems are now well known. Advantages include low non-specific chemiluminescence as the result of non-enzymatic hydrolysis, and, in the case of the 1,2-dioxetane "glow" reagents, a significantly greater sensitivity of detection as compared to calorimetric detection. Disadvantages of chemiluminescent detection include: laborious requirements for use, limitations on sensitivity arising from the transience of chemiluminescence itself, and, the broad spectral radiance of the chemiluminescent emission which precludes the simultaneous detection of multiple analytes in a single specimen.

Fluorescence detection is theoretically capable of circumventing the disadvantages of chemiluminescent detection, however, the former has long been regarded as less sensitive than chemiluminescence owing to (i) background light ("stray" light) which exists in all fluorescence detectors because of the light source used to induce excitation, (ii) poor aqueous solubility of molecules which have a high fluorescence intensity, (iii) significant photoquenching and poor photostability in aqueous solutions, and, (iv) low rates of processing (turnover) of available fluorogenic substrates by their specific enzymes. Largely because of such limitations, fluorogenic hydrolytic enzyme substrates have been made available for biological research and clinical applications. The present invention addresses that need through the identification of novel molecular structures having physical properties which overcome the limitations of previous compounds.

Sato et al. ([1992] Chem. Pharm. Bull. 40(3):786–788) disclosed a new class of fluorogenic substrates for determination of acidic and alkaline phosphatases. They disclosed 8-hydroxypyrene-1,3,6-trisulfonic acid (HPTS, "pyranine") as a highly fluorescent compound in both acidic and alkaline environments. They also disclosed that the fluorescence intensity of pyranine is markedly quenched upon phosphorylation, and could be used as a substrate for the assay of acid and alkaline phosphatases and human serum phosphatases. However, the molecule disclosed by Sato et al. had a chemical composition consistent with the molecule being $C_{16}H_6K_5O_{13}PS_3$ 4H2O, and hence was not a halohydoxypyrene disulfonic acid (HHPDS).

Wolfbeis and Koller ([1983] Anal. Chem. 129:365–370) reported on the uses of esters of HPTS as fluorogenic substrates for esterases, however these authors neither disclosed nor suggested a halogenated variant of HPDS. Wolfbeis et al. ([1983] Anal. Chem. 314:119–124) characterized the fluorescence characteristics of HPTS as well as those of a number of other fluorescent indicators. These authors neither disclosed nor suggested a halogenated variant of hydroxypyrene compounds.

Koller ([1994] Amer. Biotech. Laboratory 13 (November) :13–15) reported on the characteristics of 1-hydroxypyrene-3,6,8-tris(dimethylsulfonamide), as well as acetates, butyrates and other long-chain fatty esters, phosphate, sulfate, galactoside, glucoside, glucuronide, and N-acetyglucosaminide derivatives thereof. However, there was no disclosure or suggestion of a halo derivative of the hydroxypyrene compounds.

Tietze and Bayer ([1937] from the Wissenschaftl Hauptlaboratorium of I. G. Garbenindustrie-Werk Leverkunsen, Printed in Germany-Druck: Metzger & Wittig, Leipzig, pp. 189–210), provided an early analysis of the chemistry and fluorometric properties of pyrene sulfoacids and derivatives thereof. In the course of describing the manufacture of 3-aminopyrene-5,8,10-trisulfoacid, the preparation of 3-chloropyrene and sulfonation thereof to 3-chloropyrene-5,8,10-trisulfoacid was mentioned. However, there was no mention or suggestion of the fluorescence or lack thereof of this compound, nor was there any mention of phosphate or other derivatives of chlorodisulfoacid as fluorogenic substrates.

In U.S. Pat. Nos. 4,585,598 and 4,614,713, fluorogenic phosphate esters of hydroxy-pyrene-trisulfonic acids were disclosed for fluorometric determination of phosphatases. The disclosed water-soluble phosphoric esters were prepared by reacting the hydroxypyrene-trisulphonic acid with a phosphorus pentahalide followed by hydrolysis of the dihalogenophosphonyloxy compound. The patent neither discloses nor suggests the use of a monohalo-hydroxypyrene-disulfonic acid as a fluorogenic substrate.

In U.S. Pat. No. 5,132,432, a class of pyrenyloxy trisulfonic acids was disclosed and their utility in a number of biological and biochemical procedures was described. The disclosure of that patent is hereby incorporated by reference. While that patent mentions a wide variety of possible substituents for the pyrenyloxy trisulfonic ester compounds, there is no disclosure or suggestion of a halo-pyrenyloxy disulfonic acid derivative substituted with a phosphate, —O-galactoside, —O-glucoside, —O-glucuronide moiety or the use of such a compound as a fluorogenic substrate.

In U.S. Pat. No. 4,844,841, a class of pyrenetrisulfonic acids useful as fluorescent lipid probes was described. There was no disclosure or suggestion of the halo-pyrene-disulfonic acid derivatives of the present invention.

In U.S. Pat. No. 5,424,440, a class of benzothiazole compounds was disclosed as being water soluble fluorogenic substrates. While chemically unrelated to the present inventions, this patent is cited and incorporated herein for its review of the state of the art.

In WO 93/15097, pyrene-(1,3,6-trisulfonic acid)-8-D-glucuronide and like compounds were disclosed as being useful fluorogenic substrates for determination of glycohydrolytic enzymes, such as -D-glucuronidase. This publication neither discloses nor suggests a halo-substituted pyrene-disulfonic acid fluorogenic substrate.

BRIEF SUMMARY OF THE INVENTION

The subject invention provides a new class of fluorogenic substrates. In a specific embodiment, these substrates are the halo-pyrene-disulfonic acids and derivatives thereof. In contrast to the previously reported pyrene trisulfonic acid derivatives, these new substrates display very high rates of conversion to products when in the presence of an appropriate enzyme. Advantageously, upon enzyme hydrolysis, these compounds produce intensely fluorescent halo-pyrene derivatives which are useful as fluorescent markers in biological and biochemical systems. Equally important, these compounds are highly stable to non-enzymatic hydrolysis, thereby enabling assay applications providing great sensitivity and broad dynamic range.

Advantageously, the compounds of the subject invention have high solubility in aqueous media, longwave excitation and highly Stokes' shifted emission wavelengths that can be used in fluorometric assays.

In a specific embodiment, the substrates of the subject invention can be represented by the structure (I):

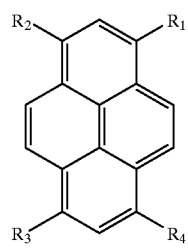

and salts thereof, wherein:

$R_1$ is O, OH, phosphate, sulfonyl, sulfate, amine, sulfonamide, ketone, ester, or a substrate for a hydrolytic enzyme (including, for example, —O-galactoside, —O-glucoside, —O-glucuronide, and N-acetylglucosaminide); and $R_2$, $R_3$, and $R_4$ are, independently, —$SO_3$, $NR_5R_6$, —$SO_2NR_5R_6$, or a halide; wherein $R_5$, and $R_6$ are independently H, aryl, heteroaryl, heterocyclo, $C_{1-6}$ alkyl, arylalkyl, heteroarylalkyl, heterocycloalkyl, or a monofunctional linker optionally linked to a detector molecule; provided that at least one of $R_2$, $R_3$, or $R_4$ is a halide.

In a preferred embodiment, one of $R_2$, $R_3$, or $R_4$ is a halide and the halide is chlorine.

In additional preferred embodiments, the substrates of the subject invention can have a formula represented by the structures (II), (III), (IV) or (V):

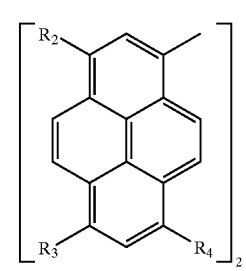

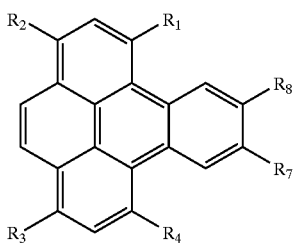

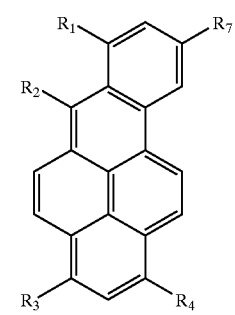

-continued

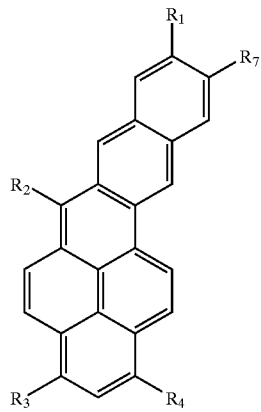

(V)

and salts thereof, wherein:

$R_1$, $R_2$, $R_3$, $R_4$, $R_7$, and $R_8$, are, independently, O, OH, phosphate, sulfonyl, sulfate, amine, sulfonamide, ketone, ester, or a substrate for a hydrolytic enzyme (including, for example, —O-galactoside, —O-glucoside, —O-glucuronide, and N-acetylglucosaminide), —$SO_3$, $NR_5R_6$, —$SO_2NR_5R_6$, halide, or aryl group; wherein $R_5$ and $R_6$ are independently H, H, aryl, heteroaryl, heterocyclo, $C_{1-6}$ alkyl, arylalkyl, heteroarylalkyl, heterocycloalkyl, monofunctional linker optionally linked to a detector molecule; provided that at least one of $R_1$, $R_2$, $R_3$, $R_4$, $R_7$, or $R_8$ is O, OH, phosphate, sulfonyl, sulfate, amine, sulfonamide, ketone, ester, or a substrate for a hydrolytic enzyme (including, for example, —O-galactoside, —O-glucoside, —O-glucuronide, and N-acetylglucosaminide).

DETAILED DISCLOSURE OF THE INVENTION

Figure 1:
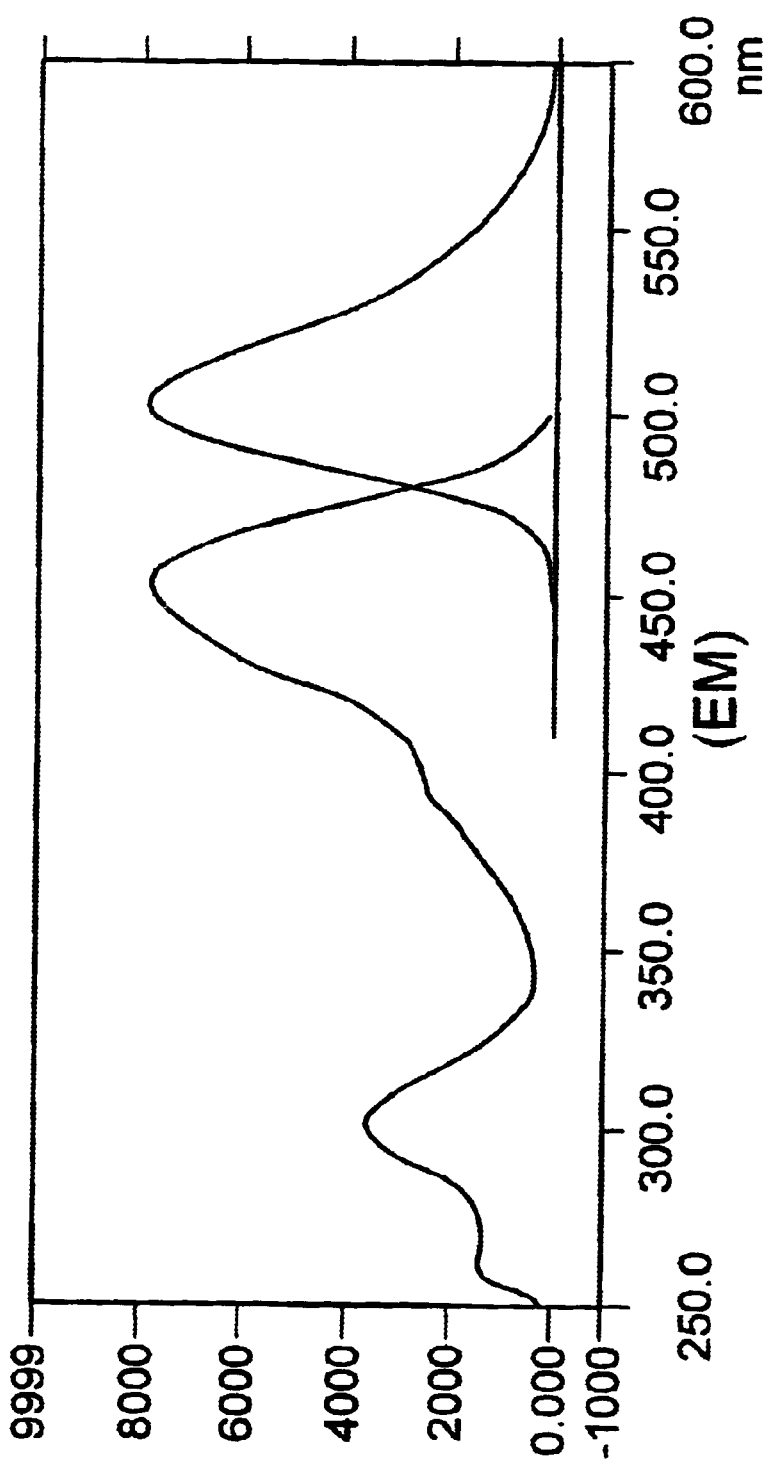
FIG. 1 shows the excitation and emission spectra of a fluorogenic substrate of this invention before and after conversion of the fluorogenic substrate to a fluorescent product.

The subject invention provides fluorogenic substrates for hydrolytic enzymes which, upon appropriate treatment, give rise to a highly fluorescent product. The fluorescent product or the fluorogenic substrate of this invention may be used in any assay in which radioisotopes or known fluorogenic molecules are currently used. Thus, for example, ELISA assays, nucleic acid detection assays, and other diagnostic assays known in the art benefit from use of the compounds disclosed herein.

For a fluorogenic substrate to be most useful in meeting the detection and labeling needs and to replace radioisotopes, it is necessary for the molecule liberated from the substrate to be highly fluorescent. Preferably, the molecule exhibits at least the following characteristics:

1. The fluorogenic substrate should have a large quantum yield. That is, the molecule should re-emit a substantial fraction of the energy. In a preferred embodiment, the molecule emits at least about 70% of the energy of the incident radiation that is used to excite the molecule. In a more preferred embodiment, the re-emitted light is about 80% or more, and in a most preferred embodiment, the re-emitted light is 90% or more.

2. The fluorogenic substrate should exhibit a large Stokes' shift. That is, the molecule should optimally be excited at a first excitation wavelength, while emitting radiation at a second emission wavelength that differs by at least about 25 nm. Preferably, the difference in wavelengths is about 35 nm. Only in this way can there be clean detection of photons derived from fluorescence, rather than the excitation photons.

3. The fluorogenic substrate should be highly soluble in aqueous media. As most biological and biochemical reactions occur, or are conducted in, water-based solutions, this is an important requirement.

4. The fluorogenic substrate should be very stable. That is, there should be very low non-specific hydrolysis of the molecule. This, too, is an important requirement, as even low levels of non-specific hydrolysis will result in unacceptable levels of background if the molecule is sufficiently fluorescent.

5. The rate of conversion of the fluorogenic substrate to its fluorescent state should be extremely rapid. This requirement is important because, even though the product may be highly fluorescent, this is useless unless a sufficient quantity of the fluorescent species is generated in a reasonably short period of time.

6. The excitation and emission spectra of the fluorogenic substrate should be narrow. This requirement is important because it enables the fluorescent product to be distinguished from other fluorophores in the same sample. This is useful in reducing background from fluorescence from other sources and for enabling the detection of multiple analytes in the same sample.

In one embodiment, the fluorogenic substrates of the subject invention have the general formula represented by structure (I):

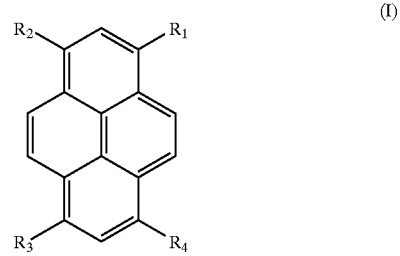

(I)

and salts thereof, wherein:

$R_1$ is O, OH, phosphate, sulfonyl, sulfate, amine, sulfonamide, ketone, ester, or a substrate for a hydrolytic enzyme (including, for example, —O-galactoside, —O-glucoside, —O-glucuronide, and N-acetylglucosaminide); and $R_2$, $R_3$, and $R_4$ are, independently, —$SO_3$, $NR_5R_6$, —$SO_2NR_5R_6$, or halide; wherein $R_5$ and $R_6$, are independently H, aryl, heteroaryl, heterocyclo, $C_{1-6}$ alkyl, arylalkyl, heteroarylalkyl, heterocycloalkyl, or a monofunctional linker optionally linked to a detector molecule; provided that one of $R_2$, $R_3$, or $R_4$ is halide.

In a preferred embodiment, the halide is chlorine.

In other preferred embodiments, the substrates of the subject invention can have a formula represented by the structures (II), (III), (IV) or (V):

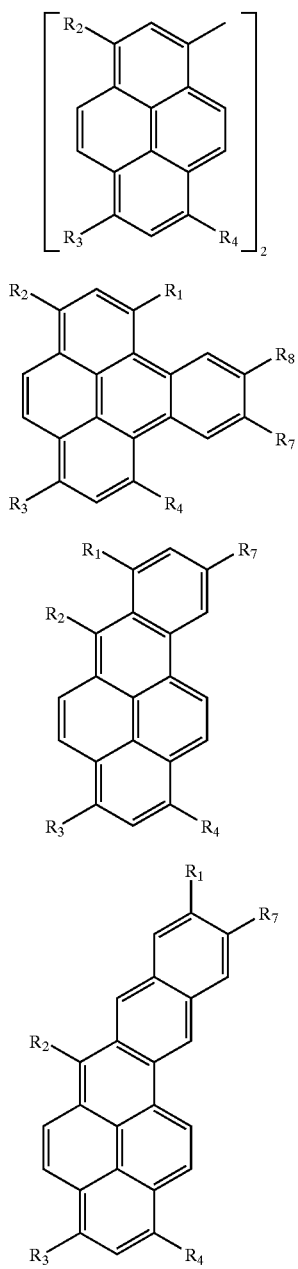

and salts thereof, wherein:

$R_1$, $R_2$, $R_3$, $R_4$, $R_7$, and $R_8$ are, independently, O, OH, phosphate, sulfonyl, sulfate, amine, sulfonamide, ketone, ester, or a substrate for a hydrolytic enzyme (including, for example, —O-galactoside, —O-glucoside, —O-glucuronide, and N-acetylglucosaminide), —$SO_3$, $NR_5R_6$, —$SO_2NR_5R_6$, halide, or aryl group; wherein $R_5$ and $R_6$ are independently H, H, aryl, heteroaryl, heterocyclo, $C_{1-6}$ alkyl, arylalkyl, heteroarylalkyl, heterocycloalkyl, monofunctional linker optionally linked to a detector molecule; provided that at least one of $R_1$, $R_2$, $R_3$, $R_4$, $R_7$, or $R_8$ is O, OH, phosphate, sulfonyl, sulfate, amine, sulfonamide, ketone, ester, or a substrate for a hydrolytic enzyme (including, for example, —O-galactoside, —O-glucoside, —O-glucuronide, and N-acetylglucosaminide).

The fluorogenic substrates of the instant invention meet all of the above noted requirements: They are highly water soluble. They are photostable as well as stable to non-enzymatic hydrolysis. They exhibit large valued Stokes' shifts (see FIG. 1) and narrow excitation and emission bands. The excitation and emission bands are preferably less than about 15 nm, and most preferably less than about 5 nm. In addition, given that it is known that halogenation of fluorophores can reduce their quantum yield by 10–100 fold (compare naphthalene with that of various halonaphthalenes (see Turro, N. J. [1978] *Modern Molecular Photochemistry*, The Benjamin/Cummings Publishing Co., Inc., pp. 110–111), the halogenated fluorescent products of this invention surprisingly and advantageously have extremely high quantum yields. Finally, the fluorogenic substrates of this invention are converted extremely rapidly (high processivity or turnover rate) to the fluorescent product. In one embodiment, the phosphorylated compound ($R_1$ is phosphate) is rapidly hydrolyzed to the hydroxyl, for example, by alkaline or acid phosphatase. These features of the compounds of the subject invention, in combination, result in the molecules of this invention providing a signal that is many orders of magnitude greater than that achievable by such known compounds as 4-MU on a molar or rate of production basis. In related embodiments, the —O-galactoside, —O-glucoside, —O-glucuronide or N-acetyglucosaminide derivatives are also rapidly hydrolyzed to the hydroxyl, by the respective specific enzymes.

In one embodiment of this invention, the compound is chlorophosphatepyrene-disulphonic acid (CPPD). Any of a number of salts thereof, for example pentammonium salt, may be used in various assays for the production of detectable fluorescent product. CPPD is prepared, for example, by phosphorylating and chlorinating hydroxypyrene-3,6,8-trisulfonic acid salt using a strong chlorine donor, such as $POCl_3$ and purified by any of a number of means, including reverse phase chromatography.

Figure 2:
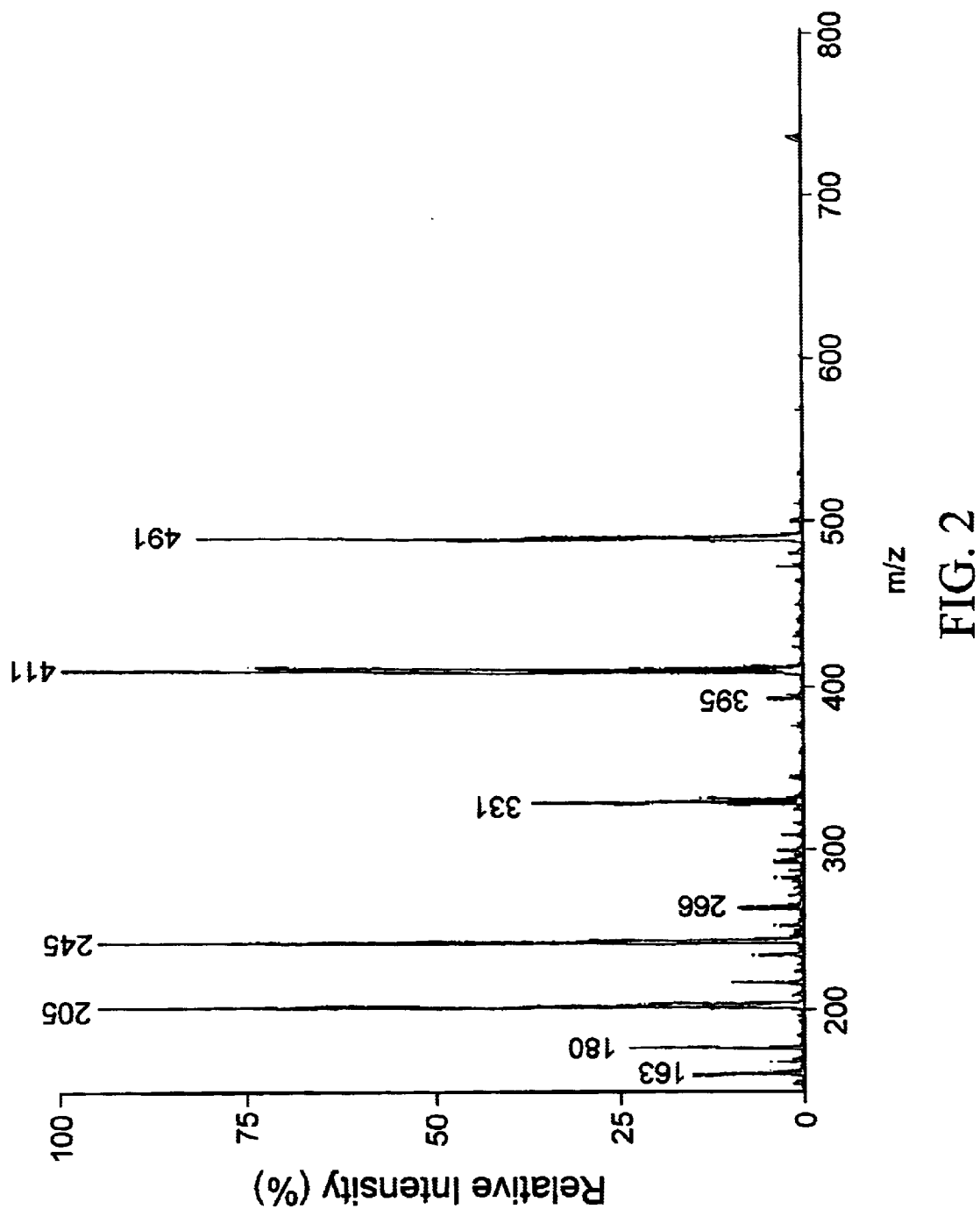
FIG. 2 is a mass spectrum of one compound of the subject invention.
Figure 3:
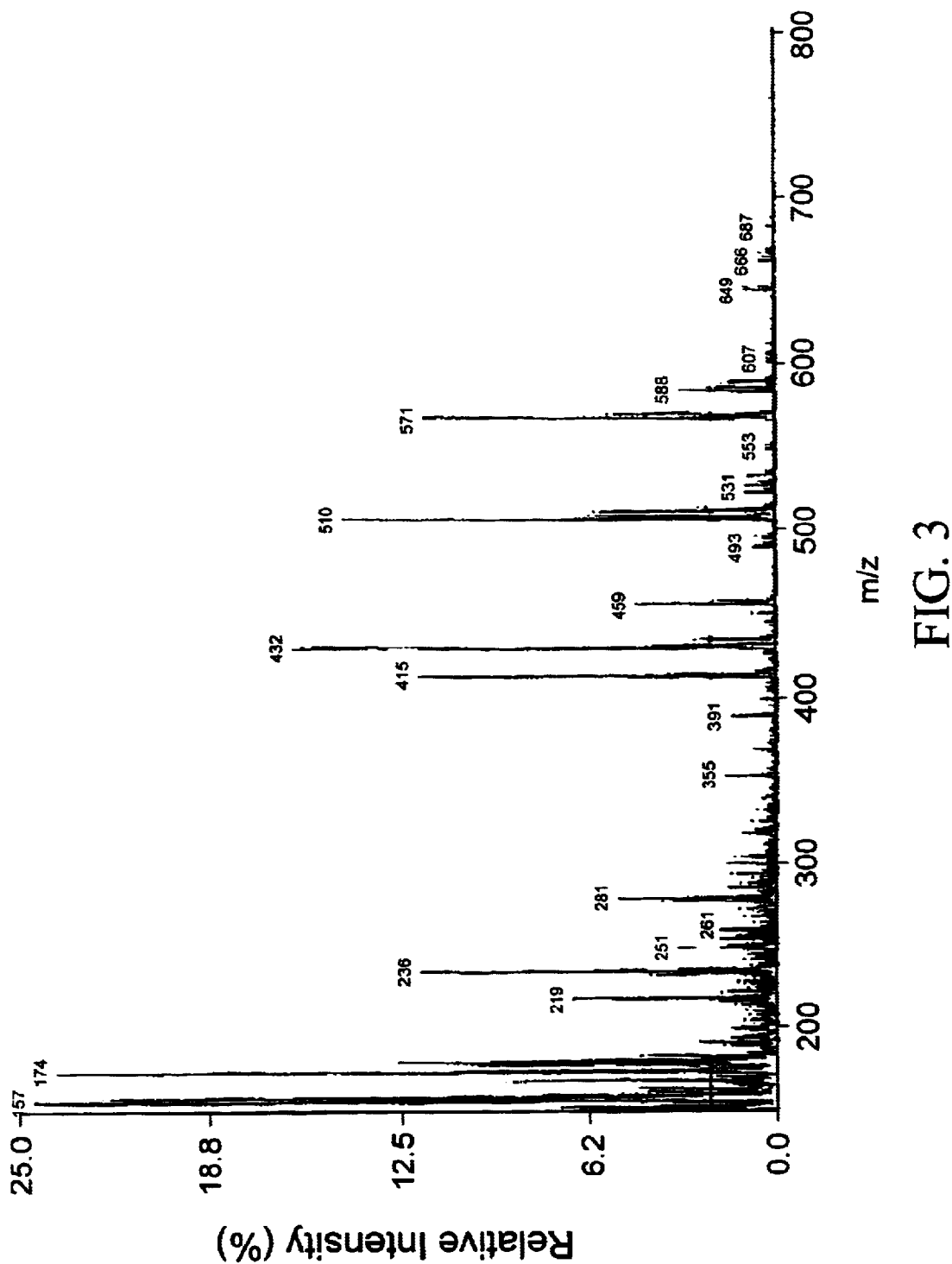
FIG. 3 is a mass spectrum of the ammonium salt of one compound of the subject invention.
Figure 4:
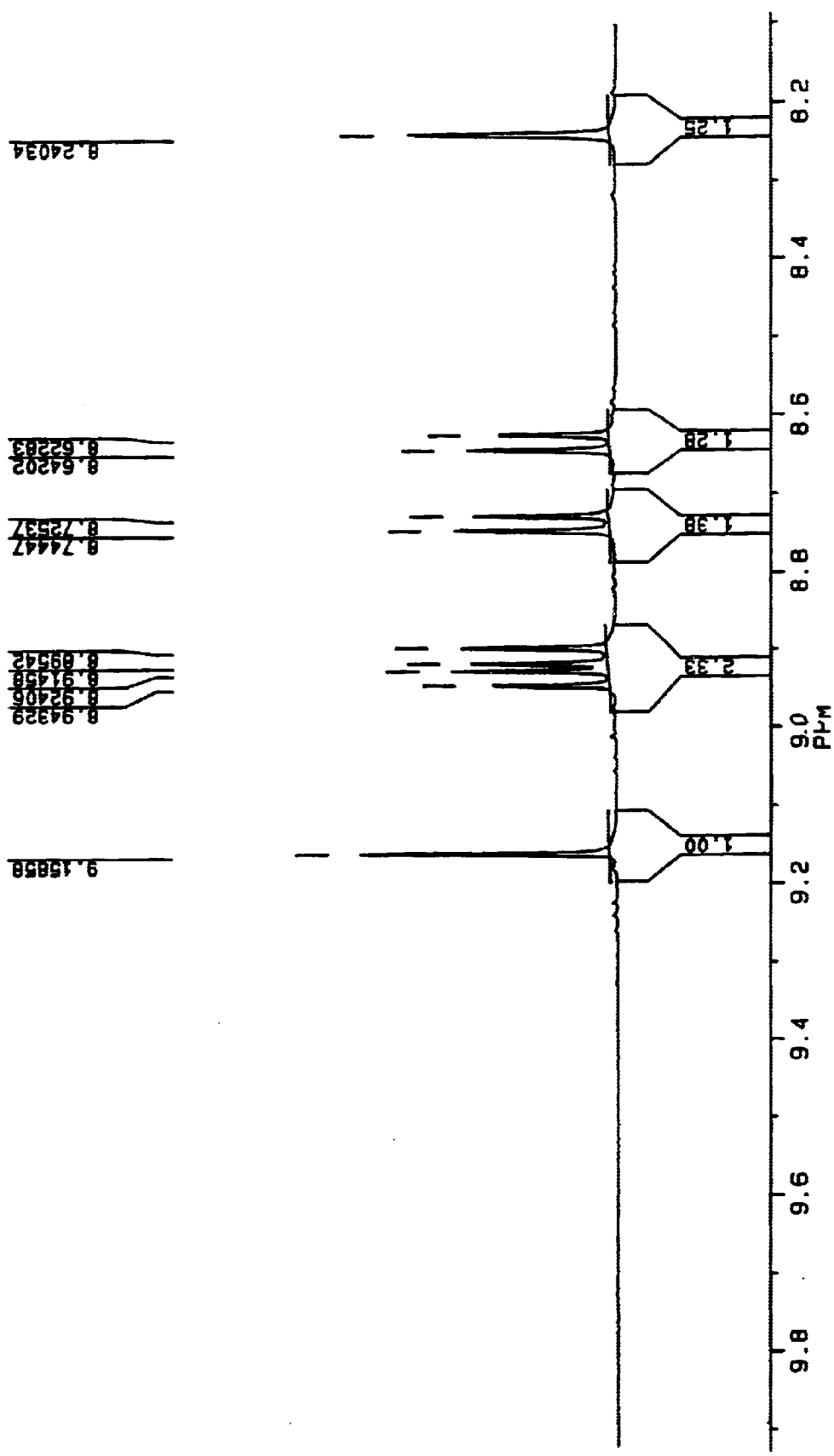
FIG. 4 is a proton NMR of one compound of the subject invention.
Figure 5:
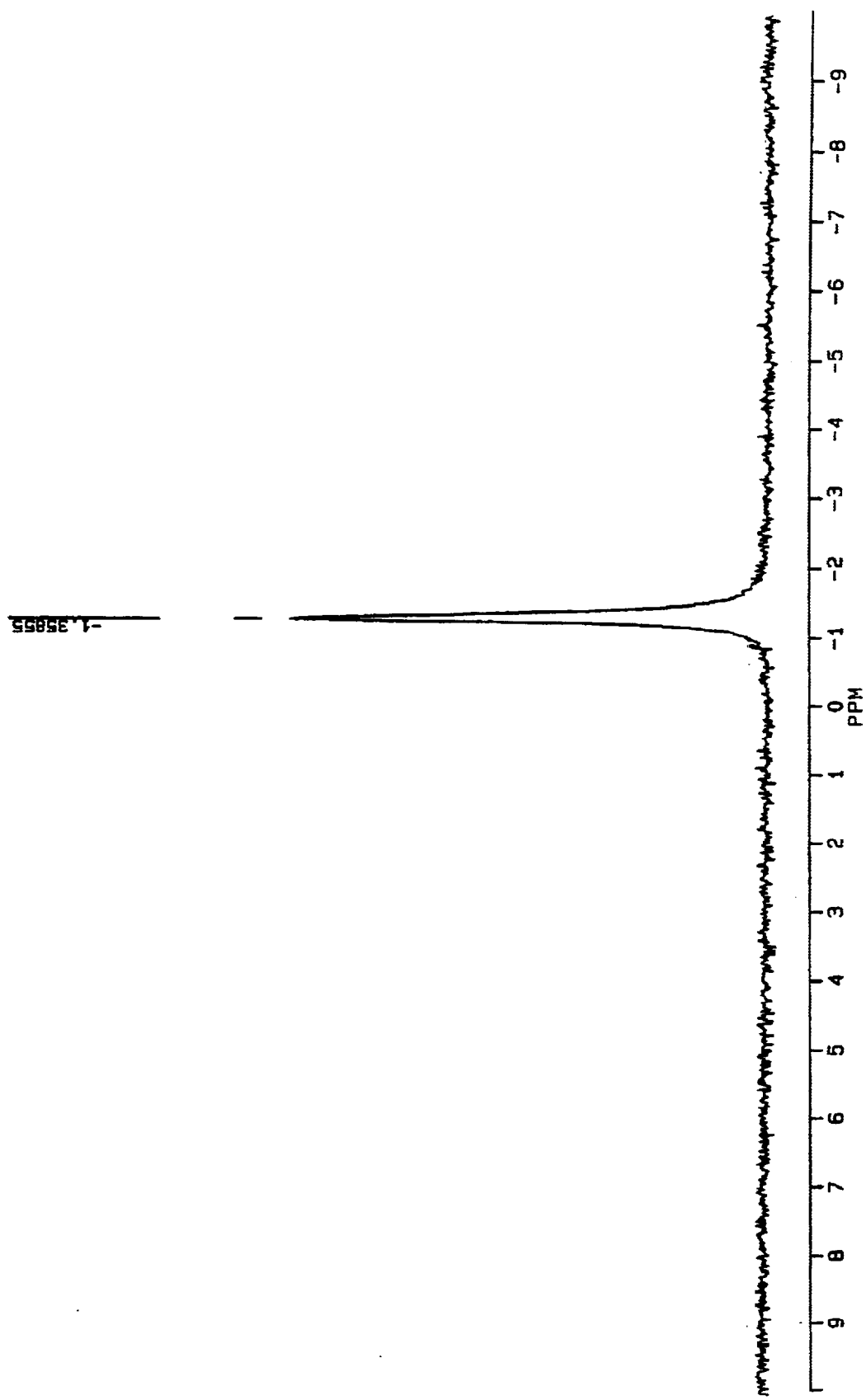
FIG. 5 is a $^{31}P$ NMR of one compound of the subject invention.

In one embodiment of this invention, the fluorogenic substrate has an elemental analysis of: C, 30.34; H, 4.55; S, 7.64; Cl, 4.36; P, 4.05. The same molecule has a mass spectrum as shown in FIG. 2, an ammonium salt mass spectrum as shown in FIG. 3; a proton NMR as shown in FIG. 4, and a $^{31}P$ NMR as shown in FIG. 5.

Those skilled in the art will recognize that the fluorogenic substrates (I) of this invention may be linked to any of a number of molecules. Accordingly, nucleic acid probes, antigens, antibodies or any other biological or chemical species could be tagged with the substrate utilizing chemical procedures which could readily be carried out by a person skilled in the art having the benefit of the instant disclosure. Upon exposure to a specific enzyme, for example a phosphatase, a glycohydrolytic enzyme or like reagent capable of hydrolyzing $R_1$ of the substrate (I), a molecule such as (VI) is produced:

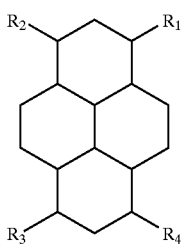

(VI)

wherein:
  $R_1$ is —OH or —O—;
  $R_2$, $R_3$, and $R_4$ are, independently, —$SO_3$, —$SO_2NH_2$, —$SON(CH_3)_2$, —Cl; provided that one of $R_2$, $R_3$ or $R_4$ is halide.

The molecule (VI) is highly fluorescent and is easily detected according to methods well known in the art.

In a particularly preferred embodiment, the compound of the subject invention has the following structure:

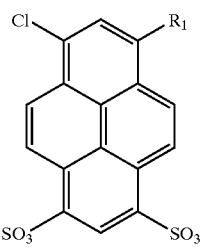

(VII)

wherein $R_1$=O or OH.

The fluorogenic substrates of the subject invention are particularly advantageous because, in a preferred embodiment, they have the following properties:

Low molecular weight, preferably below about 1,500 Daltons, and most preferably in the range of about 500–1,000 Daltons;
  2. High valued quantum yields and molar extinction coefficients;
  3. High photostability (negligible photobleaching or photooxidation);
  4. Large Stokes' shifts providing negligible photoquenching;
  5. Narrow excitation and emission bands which makes it possible to distinguish the fluorophores from others in the same specimen;
  6. High water solubility, and,
  7. High rates of processing by specific enzymes coupled with low rates of non-enzymatic hydrolysis.

The compounds of the subject invention may be supplied in a test kit or may be provided as pure compounds for use as biochemical reagents.

Following are examples which illustrate procedures for practicing the invention. These examples should not be construed as limiting. All percentages are by weight and all solvent mixture proportions are by volume unless otherwise noted.

EXAMPLE 1

Preparation of Chloro-phosphatepyrene-disulfonic Acid Pentammonium Salt, CPPD 1 g (1.9 mMole) 1-hydroxypyrene-3,6,8-trisulfonic acid trisodium salt (HPTS) and 1.59 g (6 mMole) 18-Crown-6 were suspended in 20 ml dry pyridine. After stirring at room temperature for 0.5 hour, a clear yellow solution was obtained. While cooled in an ice-water bath and with stirring, 800 μl $POCl_3$ (8.8 mmole) was added to the HPTS solution dropwise. The solution was left stirring in ice-water bath for 2 hours. After 2 hours, the reaction was checked by TLC and was found to be complete. The reaction mixture was poured over 5 ml ice and solvents were removed under reduced pressure. The residue was then dissolved in 30 ml $H_2O$. While cooling in an ice-water bath, concentrated $NH_4OH$ solution was added to bring the solution to pH 8. The solvent was then removed under reduced pressure. This process was repeated three times. The residue was then dissolved in 50 ml of water and extracted with ethyl acetate 5 times. The aqueous layer was condensed to 5 ml under reduced pressure. The yellow solution was separated from a white precipitate by centrifugation and the solid was washed with a small amount of MeOH. The solutions were combined and dried to yield 1.3 g yellow solid. The product was further purified by C18 reverse phase flash chromatography to afford 0.96 g light yellow powder (Yield: 84%).

Fluorescence: absorption max.=400 nm, emission max.=430 nm. $^1H$ NMR in $D_2O$:=8.21 (s, 1H); 8.59(d, 1H); 8.70(d, 1H); 8.91 (dd, 2H), 9.15(s, 1H). $^{31}P$ NMR in $D_2O$:=−1.99 (s). Mass Spectrum (Negative ion Electrospray with resolution of 2000): m/z=491 (M−H)$^+$, $C_{16}H_9ClO_{10}PS_2$, calculated m/z=491.

Elemental analysis expected for $C_{16}H_6ClO_{10}PS_2 \cdot 4(NH_4) \cdot 5H_2O \cdot 1.5CH_3COOH$: C, 30.06; H, 5.31; Cl, 4.67; S, 8.45; P, 4.08. Found: C, 30.34; H, 4.55; Cl, 4.36; S, 7.64; P, 4.05.

EXAMPLE 2

CPPD as a Fluorogenic Substrate of Alkaline Phosphatases With Large Stokes' Shift 1 ml of 0.01 mM CPPD solution was placed in a cuvette. The emission spectrum was recorded with excitation at 450 nm. One unit of alkaline phosphatase was then added and the solution was left at room temperature for 0.5 hour. Excitation and emission spectra were measured (see FIG. 1).

EXAMPLE 3

Kinetic Parameter Determination and Comparison to 4MUP and 4NPP

Kinetic parameters ($K_m$, $K_{cat}$) were measured in the following buffers: 50 mM TAPS pH 9.0 (CPPD); 1 M DEA pH 9.8 (4MUP and 4NPP). For CPPD and 4MUP, the parameters were measured by fluorometric assays. Fluorescence excitation and emission maxima are 440 nm and 505 nm (CPPD), and 368 nm and 448 nm (4MUP) respectively. The parameters for 4NPP were measured by colorimetric assay with the change of absorbance at 405 nm being measured. All the parameters were measured at 37° C.

For each substrate, solutions of known concentration were prepared and 1 unit of alkaline phosphatase was added. The solution was incubated at 37° C. overnight. The digested solution was then diluted to different concentrations and the relative fluorescence intensity (RFU) at 505 nm (CPPD) 410 nm (4MUP), and absorbance at 500 nm (4NPP) was measured for each solution. The data were used to prepare a plot of RFU at 505 nm (CPPD), 410 nm (4MUP), and absorbance at 500 nm (4NPP) as a function of substrate concentrations. These plots were used as standard curves to calculate the concentration of substrate being digested during enzyme assays.

For the enzyme assays, 0.001 unit of alkaline phosphatase was added to various concentrations of CPPD and 4MUP solutions. For 4NPP, 0.01 unit of alkaline phosphatase was used. After the addition of enzyme, changes in fluorescence or absorbance due to hydrolysis of substrates were automatically recorded vs. time, usually for 10 minutes. From the slope of the linear part of this plot, the activity of the enzyme was calculated and compared to the standard curve generated with completely digested substrates. $K_m$ and $K_{cat}$ were calculated from Lineweaver-Burk Plots.

EXAMPLE 4

Figure 6:
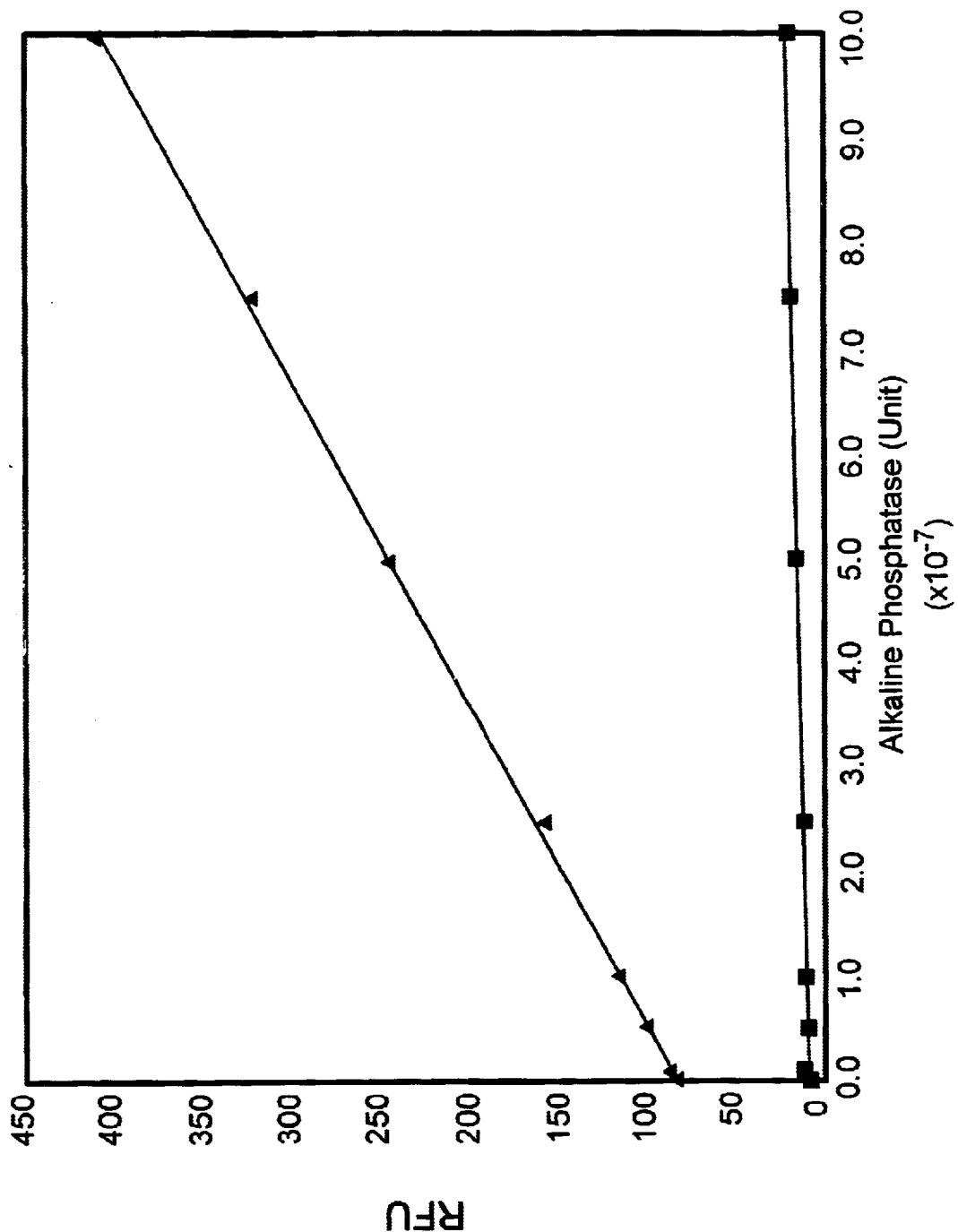
FIG. 6 illustrates the degree of detection sensitivity (alkaline phosphatase detection) achievable using a fluorogenic substrate of this invention as compared with 4-MUP.

Linear Relation of the Fluorescence Intensity vs. Enzyme Concentration and Detection Limits of Alkaline Phosphatase Using CDDP in Comparison to 4MUP 100 µl of 0.01 mM CPPD in 50 mM TAPS pH 9.0 and 0.01 mM 4MUP in 1 M DEA pH 9.8 were placed in a microtiter plate. At time zero, 10 µl of different concentrations of enzyme was added to each of a series of wells in triplicate for each enzyme concentration. The plate was incubated at 37° C. for 60 minutes and the increase in fluorescence due to enzyme hydrolysis of the substrate was measured (see FIG. 6).

EXAMPLE 5

Figure 7:
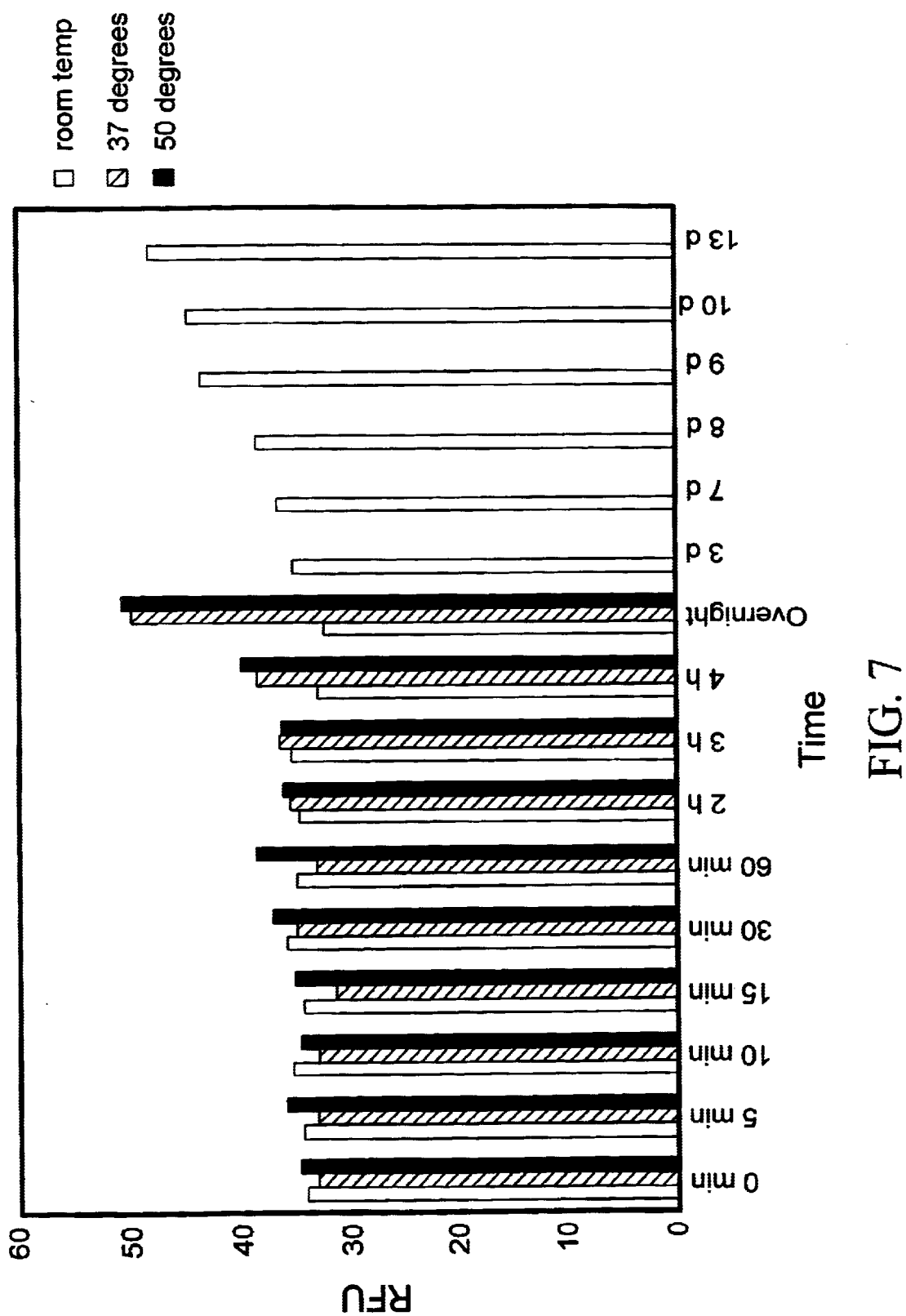
FIG. 7 shows fluorescence of CPPD at 535 nm measured at time points.

Non-enzymatic Hydrolysis of CPPD 0.1 mM CPPD in 50 mM TAPS was incubated at room temperature, 37° C. and 50° C. Fluorescence at 535 nm was measured at time points as specified in FIG. 7.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A fluorogenic substrate molecule having the following characteristics:
   (a) said molecule re-emits at least about 70% of the energy of the incident radiation that is used to excite the molecule;
   (b) the molecule emits radiation at a wavelength that is at least about 25 nm from the wavelength of radiation used to excite the molecule; and
   (c) the molecule is soluble and stable in water;
and wherein said molecule has the following structure:

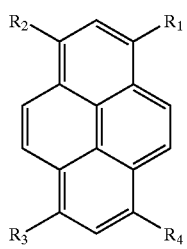

and salts thereof, wherein:
   $R_1$ is selected from the group consisting of phosphate, sulfonamide, —O-galactoside, —O-glucoside, —O-glucuronide, and N-acetylglucosaminide; and
   $R_2$, $R_3$, and $R_4$, can be the same or different, and are selected from the group consisting of $SO_3$ and halides; provided that at least one of $R_2$, $R_3$, or $R_4$ is a halide.

2. The fluorogenic substrate molecule, according to claim 1, wherein said molecule has the following structure:

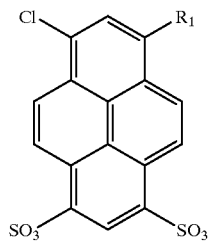

wherein $R_1$ is selected from the group consisting of phosphate, sulfonamide, —O-galactoside, —O-glucoside, —O-glucuronide, and N-acetylglucosaminide.

3. The fluorogenic substrate molecule, according to claim 1, wherein said halide is chlorine.

4. The fluorogenic substrate molecule, according to claim 1, wherein said molecule has a molecular weight in the range of about 500 to about 1000 Daltons.

5. A method of detecting a molecule of interest, wherein said molecule is labeled with a fluorogenic substrate molecule which has the following characteristics:
   (a) said molecule re-emits at least about 70% of the energy of the incident radiation that is used to excite the molecule;
   (b) the molecule emits radiation at a wavelength that is at least about 25 nm from the wavelength of radiation used to excite the molecule; and
   (c) the molecule is soluble and stable in water;
and wherein said molecule has the following structure:

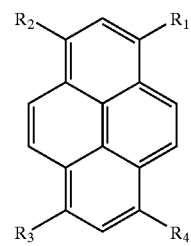

and salts thereof, wherein:
   $R_1$ is selected from the group consisting of phosphate sulfonamide, and substrates for hydrolytic enzymes; and
   $R_2$, $R_3$, and $R_4$ are, independently, selected from the group consisting of $SO_3$ and halides; provided that at least one of $R_2$, $R_3$, or $R_4$ is a halide;

and wherein said method comprises labeling a molecule of interest with said fluorogenic substrate molecule, adding an enzyme to hydrolyze said fluorogenic substrate, and detecting a change in fluorescence.

6. The method, according to claim 5, wherein said assay is selected from the group consisting of ELISAs and nucleic acid detection assays.

7. The method, according to claim 5, wherein said molecule has the following structure:

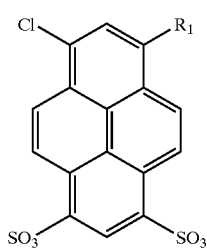
wherein $R_1$ is selected from the group consisting of phosphate, sulfonamide, —O-galactoside, —O-glucoside, —O-glucuronide, and N-acetylglucosaminide.
8. The method, according to claim 5, wherein said halide is chlorine.
9. The method, according to claim 5, wherein said molecule has a molecular weight in the range of about 500 to about 1000 Daltons.
* * * * *

UNITED STATES PATENT AND TRADEMARK OFFICE
CERTIFICATE OF CORRECTION

PATENT NO. : 6,635,435 B1
DATED : October 21, 2003
INVENTOR(S) : Conrad

It is certified that error appears in the above-identified patent and that said Letters Patent is hereby corrected as shown below:

<u>Column 10,</u>
Line 46, "(...Kcat'...)" should read -- (...Kcat...) --

Signed and Sealed this

Eighth Day of June, 2004

JON W. DUDAS
*Acting Director of the United States Patent and Trademark Office*